(12) United States Patent
Perez et al.

(10) Patent No.: US 9,574,170 B2
(45) Date of Patent: Feb. 21, 2017

(54) SCHISTOSE MICROFIBRILLATED ARTICLE FOR CELL GROWTH

(75) Inventors: Mario A. Perez, Burnsville, MN (US); Terry R. Hobbs, St. Paul, MN (US); Stephanie J. Moeller, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 2218 days.

(21) Appl. No.: 12/364,548

(22) Filed: Feb. 3, 2009

(65) Prior Publication Data

US 2009/0137044 A1 May 28, 2009

Related U.S. Application Data

(63) Continuation of application No. 11/278,616, filed on Apr. 4, 2006, now abandoned.

(51) Int. Cl.
*C12N 1/14* (2006.01)
*C12N 1/20* (2006.01)
*C12N 5/071* (2010.01)
*C12N 11/08* (2006.01)
*C12N 5/00* (2006.01)

(52) U.S. Cl.
CPC . *C12N 1/14* (2013.01); *C12N 1/20* (2013.01); *C12N 5/0068* (2013.01); *C12N 11/08* (2013.01); *C12N 2533/40* (2013.01)

(58) Field of Classification Search
USPC ........................................................ 435/395
See application file for complete search history.

(56) References Cited

U.S. PATENT DOCUMENTS

| | | | |
|---|---|---|---|
| 5,108,428 | A | 4/1992 | Capecchi et al. |
| 5,254,471 | A | 10/1993 | Mori et al. |
| 5,565,210 | A | 10/1996 | Rosenthal et al. |
| 5,792,469 | A | 8/1998 | Tipton et al. |
| 5,856,367 | A | 1/1999 | Barrows et al. |
| 6,110,588 | A | 8/2000 | Perez et al. |
| 6,252,129 | B1 | 6/2001 | Coffee |
| 6,331,343 | B1 | 12/2001 | Perez et al. |
| 6,420,024 | B1 | 7/2002 | Perez et al. |

(Continued)

FOREIGN PATENT DOCUMENTS

| | | |
|---|---|---|
| EP | 1 136 510 | 9/2001 |
| EP | 0 891 783 B1 | 6/2002 |

(Continued)

OTHER PUBLICATIONS

US 4,476,226, 10/1984, Hansen et al. (withdrawn)

(Continued)

*Primary Examiner* — Sharmila G. Landau
*Assistant Examiner* — Sheridan Macauley
(74) *Attorney, Agent, or Firm* — Kent S. Kokko

(57) ABSTRACT

The present invention relates to culturing cells utilizing a matrix of microfibrillated thermoplastic polymeric materials. More specifically, the present invention relates to a method of culturing cells. In addition, the invention relates to a biaxially oriented microfibrillated article for culturing cells dispersed in a cell culture medium. The matrix of thermoplastic polymeric materials for culturing cells of this invention finds use in tissue engineering and wound healing applications.

13 Claims, 1 Drawing Sheet

100 μm

(56) References Cited

U.S. PATENT DOCUMENTS

| | | |
|---|---|---|
| 6,432,532 B2 | 8/2002 | Perez et al. |
| 6,468,451 B1 | 10/2002 | Perez et al. |
| 6,579,537 B2 | 6/2003 | Seelich et al. |
| 6,586,073 B2 | 7/2003 | Perez et al. |
| 6,630,231 B2 | 10/2003 | Perez et al. |
| 6,645,618 B2 | 11/2003 | Hobbs et al. |
| 6,646,019 B2 | 11/2003 | Perez et al. |
| 6,680,144 B2 | 1/2004 | Choi |
| 6,692,823 B2 | 2/2004 | Kody et al. |
| 6,753,080 B1 | 6/2004 | Sebastian et al. |
| 6,890,649 B2 | 5/2005 | Hobbs et al. |
| 6,977,113 B2 | 12/2005 | Kody et al. |
| 7,195,814 B2 | 3/2007 | Ista et al. |
| 2002/0005600 A1* | 1/2002 | Ma ............................ 264/49 |
| 2002/0133229 A1* | 9/2002 | Laurencin et al. ........ 623/13.17 |
| 2002/0172816 A1 | 11/2002 | Perez et al. |
| 2002/0192449 A1 | 12/2002 | Hobbs et al. |
| 2003/0069369 A1 | 4/2003 | Belenkaya et al. |
| 2003/0211130 A1 | 11/2003 | Sanders et al. |
| 2005/0095695 A1 | 5/2005 | Shindler et al. |
| 2005/0249791 A1 | 11/2005 | Hobbs et al. |
| 2006/0049386 A1 | 3/2006 | Kody et al. |

FOREIGN PATENT DOCUMENTS

| | | |
|---|---|---|
| WO | WO 00/53721 A1 | 9/2000 |
| WO | WO 01/60335 A2 | 8/2001 |
| WO | WO 01/85226 A1 | 11/2001 |
| WO | WO 2004/071546 | 8/2004 |
| WO | WO 2006/037022 | 4/2006 |

OTHER PUBLICATIONS

Ratner et al., 2004, Annu. Rev. Biomed., 6, 41-75.*
Kim et al., 1998, Trends in Biotechnology, 16, 224-230.*
Dictionary.com, Definition of "Schistose", Accessed Sep. 6, 2013, [Online at http://dictionary.reference.com/browse/schistose], 1 pg.*
Dictionary.com, Definition of "Schist", Accessed Sep. 6, 2013, [Online at http://dictionary.reference.com/browse/schist], 1 pg.*
Mikos, et al., "Preparation and characterization of poly(l-lactic acid) foams," Polymer, vol. 35, No. 5, pp. 1068-1077, Mar. 1, 1994.
Liu, et al., "Pectin/poly(lactide-co-glycolide) composite matrices for biomedical applications, " Biomaterials, vol. 25, No. 16, pp. 3201-3210, Jul. 1, 2004.
Supplementary European Search Report for Application No. EP 07759934.
Andersson, Ann-Sofie, et al., "Nanoscale features influence epithelial cell morphology and cytokine production," Elsevier, Biomaterials vol. 24, 2003, pp. 3427-3436.
Crouch, Adam, et al., "Correlation of anisotropic cell behaviors with topographic aspect ratio," Elsevier, Biomaterials vol. 30, 2009, pp. 1560-1567.
Drury, Jeanie L. and David J. Mooney, "Hydrogels for Tissue Engineering: Scaffold Design Variables and Applications," Elsevier; Biomaterials vol. 24, 2003; pp. 4337-4351.
Kidoaki, K., et al; "Mesoscopic Spatial Designs of Nano- and Microfiber Meshes for Tissue-Engineering Matrix and Scaffold Based on Newly Devised Multilayering and Mixing Electrospinning Techniques," Elsevier; Biomaterials vol. 26, 2005; pp. 37-46.
Martinez, E., et al., "Effects of artificial micro-and nano-structured surfaces on cell behaviour," Elsevier, Annuals of Anatomy vol. 191, 2009, pp. 126-135.
Seal, B.L., et al., "Polymeric biomaterials for tissue and organ regeneration," Materials Science and Engineering, R. 34, 2001, pp. 147-230.
"Section IV: Technical Information," ATCC, [retrieved from the internet Mar. 2006] www.atcc.org; pp. 242-259.
Sodian, Ralf, et al., "Evaluation of biodegradable, three-dimensional matrices for tissue engineering of heart valves," ASAIO Journal, vol. 46, Issue 1, Jan./Feb. 2000.
Wikipedia, "Units of Textile Measurement," retrieved from the internet on Sep. 8, 2008, http://en.wikipedia.org/wiki/Units_of_textile_measurement#Denier, p. 1-3.
Doshi, Jayesh, et al., "Electrospinning Process and Applications of Electrospun Fibers," Elsevier, Journal of Electrostatics, vol. 35, 1995, pp. 151-160.
Kumbar, S.G., et al., "Electrospun nanofiber scaffolds: engineering soft tissues," Biomedical Materials, vol. 3, No. 3, Sep. 2008, p. 34002, 15 pages.
Sanders, J.E., et al., "Fibrous encapsulation of single polymer microfibers depends on their vertical dimension in subcutaneous tissue," Journal of Biomedical Materials Reserch—Part A, vol. 67, No. 4, Dec. 15, 2003, pp. 1181-1187.

* cited by examiner

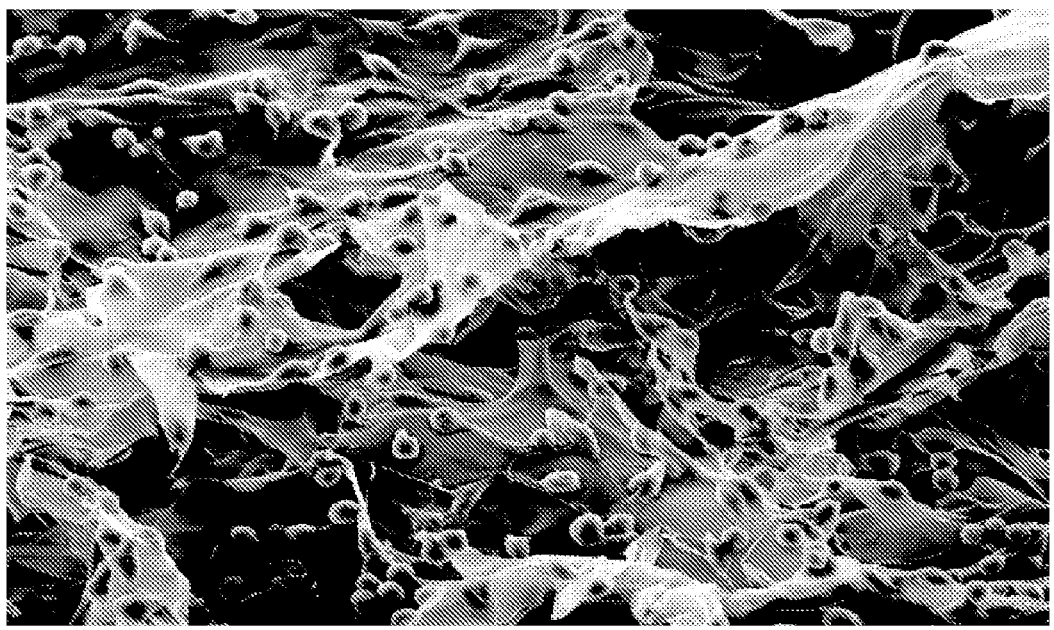

SCHISTOSE MICROFIBRILLATED ARTICLE FOR CELL GROWTH

CROSS REFERENCE TO RELATED APPLICATIONS

This application is a continuation of U.S. application Ser. No. 11/278,616, filed Apr. 4, 2006, now abandoned, the disclosure of which is incorporated by reference in its entirety herein.

FIELD

The present invention relates to culturing cells utilizing a matrix of microfibrillated thermoplastic polymeric materials.

BACKGROUND

Tissue engineering and wound healing are approaches to reconstruction and/or regeneration of lost or damaged tissue. Earlier efforts at developing extracellular matrices for cell growth have included the use of biodegradable and bioabsorbable materials. In the development of these matrices, hyaluronic acid and collagen have been employed for use as engineering tissues in the replacement of organs, skin replacements for burns or ulcers, replacement of bone loss or even replacement of brain tissue. These materials are typically expensive and have variable properties when produced in large quantities.

Polymers such as polylactic acid homopolymers and polycaprolactone homopolymers, and their related copolymers and blends provide a porous structure for cell penetration and polymer degradation as scaffolds and/or extracellular matrices. However, for successful tissue regeneration, sufficient cell propagation and appropriate differentiation must be achieved in a three-dimensional cellular composite. Nonwoven fabrics have been used as scaffolds in tissue applications as described in Aigner, J. et al., "Cartilage Tissue Engineering with Novel Nonwoven Structured Biomaterial Based on Hyaluronic Acid Benzyl Ester", *J. Biomed. Mater. Res.*, 1998, 42, 172-181; Bhat, G. S., "Nonwovens as Three-Dimensional Textiles for Composites", *Mater. Manuf. Process*, 1995, 10, 67-688; Ma, T., "Tissue Engineering Human Placenta Trophoblast Cells in 3-D Fibrous Matrix: Spatial Effects on Cell Proliferation and Function", *Biotechnol. Prog.*, 1999, 15, 715-724, and Bhattarai, S. R. et al., "Novel Biodegradable Electrospun Membrane: Scaffold for Tissue Engineering", *Biomaterials*, 2004, 25, 2595-2602.

Cell biology entails the structure and function of cells, the basic units that make up living organisms. The form and function of the human body are the sum of the form, function, and behavior of its component cells. As a result, research in this area has grown to better understand the prevention and treatment of disease and human behavior. Technology and methodology improvements have evolved cell biology to new levels of understanding cells.

In a growing cellular system, a cycle occurs from the formation of a cell by the division of the mother cell into two daughter cells. This cycle occurs in multicellular organisms as well as in cultures of isolated cells. All of the components of the cell double during the cycle ending with the splitting events of mitosis (nuclear division) and cytokinesis (cytoplasmic division).

Cells in a multicellular organism become specialized to perform specific functions via cell differentiation. The life cycle of a higher organism begins with a unicellular stage, and becomes more complex as the individual grows and takes on its characteristic form. Differentiated cells maintain their characteristic form and identity because populations of specialized cell types remain assembled in a certain pattern. Several cell types make up a tissue, and different tissues build an organ.

The movement of cells and their cellular components are relative to its environment. The extremely diverse movements as a form of locomotion are analogous to those of amoebas. This intracellular movement is accomplished by the formation of pseudopodia, in which cytoplasm streams actively during pseudopod extension and withdrawal. In some cases, the cells are known to exert forces that change the shape of developing tissues and organs of embryos. The cells crawl through body cavities, lymph channels, and tissue spaces to seek out and engulf bacteria, foreign matter, and dead or dying cells. In wound healing activities, the adjacent cells crawl across the wound surface, covering it while other cells infiltrate and fill in the gaps. Tissue cells crawl very slowly at a speed of about 0.5 to 50 micrometers/minute, whereas, structural cells such as fibroblasts advance their own length in an hour or so, moving approximately 1 to 2 mm/day. More information about cells and cell biology can be found in *McGraw-Hill Encyclopedia of Science & Technology*, 1987, 3, 317-384.

In developing a matrix for cell growth, cell differentiation and proliferation is often difficult with respect to conventional culture techniques. The cultured cells normally are isolated from their tissue specific extracellular matrix followed by suspension in a growth medium where they adhere to the bottom of a culture dish to form a confluent monolayer. Cells often lose their morphology as well as their biochemical and functional properties. As a result, dedifferentiated cells may behave differently compared to their original tissue environment. In order for cellular proliferation and differentiation on to occur, attachment must occur to the scaffold with sufficient surface area. The scaffold or matrix surface may be modified with a peptide sequence to promote recognition and rapid adhesion of the cells. Furthermore, the three dimensional matrix requires a porous structure which can allow nutrients and gases to diffuse into a mass of cells attached to the flakes. The free exchange of nutrients, gases and waste to and from the cells proliferating throughout the scaffold is necessary to maintain cell viability. This allows the matrix to act as a carrier for the differentiation and proliferation for extended periods of time.

SUMMARY

The present invention is directed to an article and method of culturing cells. In one aspect, a method of culturing cells is provided which comprises a matrix of biaxially oriented, thermoplastic substrate having a schistose structure dispersed in a cell culture medium, and inoculating the matrix with cells. The schistose surface comprises microflakes having an average length of less than 20 micrometers, and generally from 1 to 3 micrometers. The average width of the microflakes is less than 200 micrometers, and generally 5 to 30 micrometers. The microflakes have an average thickness of 1 to 20 micrometers with an aspect ratio of the surface of 1:1 to 1:20. The surface area of the microflakes is greater than 0.5 $m^2$/gram. The microflakes of this invention tend to be generally parallel to one another, and are shaped like a plate or a plate-like ribbon favoring cell attachment with a greater surface area. The stiffness and three-dimensional structure of the flakes in the matrix allows the cells to retain their differentiation and proliferation ability.

In another aspect, the invention provides a microfibrillated article for culturing cells, the article comprising a thermoplastic polymer film having an integral matrix of biaxially oriented, thermoplastic microflakes from a schistose surface, where the microfibrillated article is dispersed within a cell culture medium. The microflakes of the substrate are integral to a depth of 10 micrometers or greater in a microfibrillated article located on at least one surface of a thermoplastic film. Alternatively, the microfibrillated article may have a microfibrillated morphology throughout the entire thickness of the thermoplastic film.

The invention provides for cells that are inoculated onto the schistose surface of the matrix of microflakes, where the matrix is immersed in a cell culture medium. The cell culture medium may contain cells from various cell lines. Further, the invention comprises an article of a film having at least one microfibrillated schistose surface where the cell growth matrix is a tissue scaffold. Also, the invention comprises a microfibrillated article which is a matrix for a multi-well device or vessel.

The above summary of the present invention is not intended to describe each disclosed embodiment or every implementation of the present invention. The figures and the detailed description which follow, more particularly exemplify illustrative embodiments.

BRIEF DESCRIPTION OF THE DRAWINGS

FIG. 1 is a digital image of a scanning electron micrograph of the biaxially oriented, thermoplastic substrate having a schistose surface comprising microflakes dispersed in a cell culture medium of Example 3.

DETAILED DESCRIPTION

For the following defined terms, these definitions shall be applied, unless a different definition is given in the claims or elsewhere in the specification.

The term "microfibrillated article" is defined as a biaxially oriented, thermoplastic film, sheet or foam which has been microfibrillated by imparting sufficient fluid energy to disrupt the surface. The resulting schistose microfibrillated surface comprises a matrix of biaxially oriented thermoplastic microflakes prepared from biaxially oriented film substrates. Optionally, the microflakes may be harvested from the microfibrillated surface of the film.

The term "microfibrillated surface" is a surface that includes microflakes derived from one or more layers of a microfibrillatable material. The microflakes are portions of the oriented thermoplastic film that have been at least partially mechanically separated or fragmented from the continuous film as result of the microfibrillation. The size and shape of the microflakes typically have dimensions as a function of the type of microfibrillatable material and its physical and chemical properties, such as the type and degree of orientation, the presence and size of voids, multiple layers, layer thickness, and spherulites, not to be all inclusive. The microflakes preferably remain attached to the microfibrillated material at one end, but may also become completely detached from the base film.

The term "microflake" is a microfibrillated structure comprising a schistose structure. The microflakes tend to be generally parallel to one another, are shaped like a plate or a plate-like ribbon where the length scale of two of the microflakes' planar (width and length) dimensions is at least 10 times, preferably at least 20 times, the length scale of the microflake's third (thickness) dimension. The flakes can be connected to one another and tend to be continuous in a width or length direction. Dimensions can be measured using a scanning electron microscope.

The term "voided film" may be a thermoplastic polymeric microvoided film, or a voided film prepared from an immiscible mixture of an a semicrystalline polymer and a void-initiating component. The term "voided" shall include "microvoided". As used herein, the term, "film" shall encompass sheets, including foamed and voided sheets and it may also be understood that other configurations and profiles such as tubes may be provided with a microfibrillated schistose surface with equal facility.

The term "cell line" is a culture of cells that grow and replicate continuously under favorable conditions. A cell line originates from cell cultures with a limited lifetime, and can be cultured regularly if maintained and split at required intervals.

The term "cell culture medium" is a complex mixture of salts, carbohydrates, vitamins, amino acids, metabolic precursors, growth factors, hormones, and trace elements. The medium components may vary dependent on the specific cell line of interest.

The term "complete growth medium" shall consist of a cell culture medium with added hormones, trace elements, growth factors and sera. It is a substance to maintain the viability of cells or microorganisms.

"Cultured cells" are defined as cells growing in a synthetic environment, i.e. complete growth medium. For example, mammalian cells may be cultured as a function of the growth medium, pH, temperature, osmolality, and other factors. The cell culture is the growth of cells separate from the organism.

The term "harvesting of cells" is referred to as removing cells from a cell culture medium. Cell lines may anchor to a dish or flask to grow in monolayers. Cell lines may also anchor to a matrix of biaxially oriented, thermoplastic substrate having a schistose surface comprising microflakes to grow in a three dimensional structure. These cells may be subcultured at regular intervals to maintain cell viability.

The term "confluency" refers to the degree of growth of cells on a substrate.

The term "inoculating" or "seeding" refers to the act or step of placing cells on a matrix of biaxially oriented, thermoplastic substrate having a schistose surface comprising microflakes dispersed in a cell culture medium.

The term "mammalian cells" refer to various sources derived from mouse, human, monkey, and rat cell lines, not to be all inclusive.

The term "extracellular matrix" consists of a synthetic scaffold comprising a matrix of biaxially oriented, thermoplastic substrate having a schistose surface comprising microflakes for the proliferation and differentiation of cells in a three-dimensional structure.

The term "biodegradable" means that the microfibers or microfibrillated articles degrade from the action of naturally occurring microorganisms such as bacteria, fungi, algae and/or natural environmental factors.

The term "bioabsorbable" means that the microfibers or microfibrillated articles may be broken down by biochemical and/or hydrolytic processes, and absorbed by living tissue.

The term "degree or depth of microfibrillation" refers to as little as 10 micrometers, but may be up to 50 micrometers or greater, 100 micrometers or greater, up to the thickness of a completely microfibrillated film, as measured by the loft.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", an and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Not withstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

This invention provides a method for culturing cells. The method includes providing a matrix of biaxially oriented, thermoplastic substrate having a schistose surface comprising microflakes dispersed in a cell culture medium. In another embodiment, the method comprises a microfibrillated article having a schistose surface dispersed in a cell culture matrix, where the microflakes are further inoculated with cells. The microflakes have an average length of less than 20 micrometers, and a surface area greater than 0.5 m$^2$/gram.

The microfibrillated article used in this invention comprises a matrix of biaxially oriented, thermoplastic substrate having a schistose surface integral to an oriented, thermoplastic film for culturing cells in a three-dimensional array for the proliferation and differentiation of cells. The microfibrillated article provides cell attachment and proliferation for application in wound healing and tissue engineering applications. The biaxially oriented thermoplastic polymeric substrate comprising microflakes provides stiffness and a rectangular geometry. The manufacturing of these flakes provides for high strength, interstitial spaces between flakes and the flake geometry. The microfibrillated article is dispersed in a cell culture medium and further inoculated with cultured cells. Inoculation of the flakes with cells allows for a high density of cells and extensive spreading.

Polymers useful in forming a matrix of biaxially oriented, thermoplastic substrate having a schistose surface comprising microflakes, and the microfibrillated article include any melt-processible thermoplastic crystalline, semicrystalline or crystallizable polymer or copolymer, including block, grafted, and random copolymers. Semicrystalline polymers consist of a mixture of amorphous regions and crystalline regions. The crystalline regions are more ordered and segments of the chains actually pack in crystalline lattices. Some polymers can be made semicrystalline by heat treatments, stretching or orienting, and by solvent inducement, where these processes can control the degree of true crystallinity. Semicrystalline polymers useful in this invention include polyethylene, polypropylene, copolymers of polypropylene, copolymers of polyethylene, poly(alpha)olefins, polyoxymethylene, poly(vinylidine fluoride), poly(vinyl alcohol), poly(methylpentene), poly(ethylene-chlorotrifluoroethylene), poly(vinylfluoride), poly(ethylene oxide), poly(ethylene terephthalate), poly(butylene terephthalate), nylon 6, nylon 6,6, nylon 6,12, polybutene, poly(lactide), syndiotactic polystyrene, and thermotropic liquid crystal polymers. Preferred polyolefins include polypropylene and polyethylene that are readily available at low cost and can provide desirable properties such as high modulus and high tensile strength in microfibrillated articles.

Useful polymers preferably are those that can undergo processing to impart a high orientation ratio in a manner that enhances their mechanical integrity, and are semi-crystalline in nature. Orienting semi-crystalline polymers significantly improves the strength and elastic modulus in the orientation direction, and orientation of a semicrystalline polymer below its melting point results in an oriented crystalline phase with fewer chain folds and defects. The most effective temperature range for orienting semicrystalline polymers is between the alpha crystallization temperature of the polymer and its melting point. The alpha crystallization temperature, or alpha transition temperature, corresponds to a secondary transition of the polymer at which crystal sub-units can be moved within the larger crystal unit.

Preferred polymers in this aspect therefore are those that exhibit an alpha transition temperature ($T_{ac}$) and include, for example: high density polyethylene, linear low density polyethylene, ethylene α-olefin copolymers, polypropylene, poly(vinylidene fluoride), poly(vinyl fluoride), poly(ethylene chlorotrifluoroethylene), polyoxymethylene, poly(ethylene oxide), ethylene-vinyl alcohol copolymer, and blends thereof.

Microflakes and microfibrillated articles may also be prepared from voided, oriented films having a thermoplastic polymeric component and a void-initiating component. Such oriented, voided films are described in U.S. Pat. No. 6,331,343 (Perez et al.), U.S. Pat. No. 6,468,451 (Perez et al.) and U.S. Pat. No. 6,645,618 (Hobbs et al.), the entire disclosures of which are incorporated by reference.

When using the voided, oriented films, the thermoplastic polymeric component comprises polymers as described, including homopolymers, copolymers and blends. The thermoplastic polymeric component may further comprise small amounts of a second polymer to impart desired properties to the microfibrillated article of the invention. The second polymer of such blends may be semicrystalline or amorphous and is generally less than 30 weight percent, based of the weight of the aliphatic polyester component. Small amounts of other polymers may be added, for example, to enhance stiffness, crack resistance, Elmendorff tear strength, elongation, tensile strength and impact strength, as is known in the art.

The void-initiating component is chosen so as to be immiscible in the semicrystalline polymer component. It may be an organic or an inorganic solid having an average particle size of from about 0.1 to 20 micrometers, preferably 1 to 10 micrometers, and may be any shape including amorphous shapes, rhombohedra, spindles, plates, diamonds, cubes, and spheres.

Useful inorganic solids useful as void initiating components include solid or hollow glass, ceramic or metal particles, microspheres or beads; zeolite particles; inorganic compounds including, but not limited to metal oxides such as titanium dioxide, alumina and silicon dioxide; metal, alkali- or alkaline earth carbonates or sulfates; kaolin, talc, carbon black and the like. Inorganic void initiating components are chosen so as to have little surface interaction, due to either chemical nature or physical shapes, when dispersed in the aliphatic polyester component In general the inorganic void initiating components should not be chemically reactive with the polymer component(s), including Lewis acid/base interactions, and have minimal van der Waals interactions.

Preferably the void initiating component comprises a thermoplastic polymer, including semicrystalline polymers and amorphous polymers, to provide a blend immiscible with a second polymeric component. An immiscible blend shows multiple amorphous phases as determined, for example, by the presence of multiple amorphous glass transition temperatures using differential scanning calorimetry or dynamic mechanical analysis. As used herein, "immiscibility" refers to polymer blends with limited solubility and non-zero interfacial tension, i.e. a blend whose free energy of mixing is greater than zero:

$$\Delta G \cong \Delta H_m > 0$$

Miscibility of polymers is determined by both thermodynamic and kinetic considerations. Common miscibility predictors for non-polar polymers are differences in solubility parameters or Flory-Huggins interaction parameters. For polymers with non-specific interactions, such as polyolefins, the Flory-Huggins interaction parameter can be calculated by multiplying the square of the solubility parameter difference with the factor (V/RT), where V is the molar volume of the amorphous phase of the repeated unit, R is the gas constant, and T is the absolute temperature. As a result, the Flory-Huggins interaction parameter between two non-polar polymers is always a positive number.

Polymers useful as the void-initiating component include the above described semicrystalline polymers, as well as amorphous polymers, selected so as to form discrete phases upon cooling from the melt. Useful amorphous polymers include, but are not limited to, polystyrene, polycarbonate, some polyolefins, cyclic olefin copolymers (COC's) such as ethylene norbornene copolymers, and toughening polymers such as styrene/butadiene rubber (SBR) and ethylene/propylene/diene rubber (EPDM).

When using an immiscible polymer blend, the relative amounts of the first thermoplastic polymeric component and void initiating polymer component may be chosen so the first thermoplastic polymer forms a continuous phase and the void initiating polymer component forms a discontinuous phase. As the amount of void initiating polymer in the blend is increased, a composition range will be reached at which the void initiating polymer can no longer be easily identified as the dispersed, or discrete, phase. Further increase in the amount of void initiating polymer in the blend will result in two co-continuous phases, then in a phase inversion wherein the void initiating polymer becomes the continuous phase. Preferably, the thermoplastic polymeric component forms the continuous phase while the void initiating component forms a discontinuous, or discrete phase, dispersed within the continuous phase of the first polymer. If the void-initiating polymer is semicrystalline and is used in amounts sufficient to form a co-continuous phase, orienting followed by microfibrillation will result is a composite structure of two different microflakes, each derived from the thermoplastic polymeric component and the void-initiating polymer.

In general, as the amount of the void initiating component increases, the amount of voiding in the final film also increases. As a result, properties that are affected by the amount of voiding in the film, such as mechanical properties, density, light transmission, etc., will depend upon the amount of added void initiating component.

Preferably, whether the void initiating component is organic or inorganic, the amount of the void initiating component in the composition is from 1% by weight to 49% by weight, more preferably from 5% by weight to 40% by weight, most preferably from 5% by weight to 25% by weight. In these composition ranges, the first thermoplastic polymer may form a continuous phase, while the void initiating component forms the discrete, discontinuous phase.

Additionally, the selected void initiating polymer component must be immiscible with the semicrystalline polymer component selected. In this context, immiscibility means that the discrete phase does not dissolve into the continuous phase in a substantial fashion, i.e., the discrete phase must form separate, identifiable domains within the matrix provided by the continuous phase.

High melt strength polypropylene foam is useful for preparing microfibrillated articles. Foamable polypropylene may consist of propylene homopolymers or may comprise a copolymer having 50 weight % or more propylene monomer content. Further, the foamable polypropylene may comprise a mixture or blend of propylene homopolymers or copolymers with a homo- or copolymer other than propylene homo- or copolymers described in U.S. Pat. No. 6,468,451 (Perez et al.).

Particularly useful propylene copolymers are those of propylene and one or more non-propylenic monomers. Propylene copolymers include random, block, and graft copolymers of propylene and olefin monomers selected from the group consisting of C3-C8 α-olefins and C4-C10 dienes. Propylene copolymers may also include terpolymers of propylene and α-olefins selected from the group consisting of C3-C8 α-olefins, wherein the α-olefin content of such terpolymers is preferably less than 45 wt. %. The C3-C8 α-olefins include 1-butene, isobutylene, 1-pentene, 3-methyl-1-butene, 1-hexene, 3,4-dimethyl-1-butene, 1-heptene, 3-methyl-1-hexene, and the like. Examples of C4-C10 dienes include 1,3-butadiene, 1,4-pentadiene, isoprene, 1,5-hexadiene, 2,3-dimethyl hexadiene and the like.

Other polymers that may be added to the high melt strength polypropylene in the foamable composition include high, medium, low and linear low density polyethylene, fluoropolymers, poly(1-butene), ethylene/acrylic acid copolymer, ethylene/vinyl acetate copolymer, ethylene/propylene copolymer, styrene/butadiene copolymer, ethylene/styrene copolymer, ethylene/ethyl acrylate copolymer, ionomers and thermoplastic elastomers such as styrene/ethylene/butylene/styrene (SEBS), and ethylene/propylene/diene copolymer (EPDM).

Aliphatic polyesters are also useful for preparing microfibrillated articles or microflakes, which include homo- and copolymers of poly(hydroxyalkanoates) and homo- and copolymers of those aliphatic polyesters derived from the reaction product of one or more alkanediols with one or more alkanedicarboxylic acids (or acyl derivatives). Miscible and immiscible blends of aliphatic polyesters with one or more additional semicrystalline or amorphous polymers may also be used.

One useful class of aliphatic polyesters is poly(hydroxyalkanoates), derived by condensation or ring-opening polymerization of hydroxy acids, or derivatives thereof.

Suitable poly(hydroxyalkanoates) may be represented by the formula H(O—R—C(O)—)$_n$—OH, where R is an alkylene moiety that may be linear or branched and n is a number from 1 to 20, preferably 1 to 12. R may further comprise one or more caternary (i.e. in chain) ether oxygen atoms. Generally the R group of the hydroxyl acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (also known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, and polycaprolactone, polyglycolic acid (also known as polyglycolide). Copolymers of two or more of the above hydroxy acids may also be used, for example, poly(3-hydroxybutyrate-co-3-hydroxyvalerate), poly(lactate-co-3-hydroxypropanoate) and poly(glycolide-co-p-dioxanone). Blends of two or more of the poly(hydroxyalkanoates) may also be used, as well as blends with one or more semicrystalline or amorphous polymers.

Another useful class of aliphatic polyesters includes those aliphatic polyesters derived from the reaction product of one or more alkanediols with one or more alkanedicarboxylic acids (or acyl derivatives). Such polyesters have the general formula:

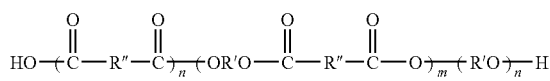

where R' and R" each represent an alkylene moiety that may be linear or branched having from 1 to 20, preferably 1 to 12 carbon atoms, and m is a number such that the ester is polymeric, and is preferably a number such that the molecular weight of the aliphatic polyester is 10,000 to 300,000 and is preferably from about 30,000 to 200,000. Each n is independently 0 or 1. R' and R" may further comprise one or more caternary (i.e. in chain) ether oxygen atoms.

Examples of aliphatic polyesters include those homo- and copolymers derived from (a) one or more of the following diacids (or derivative thereof): succinic acid, adipic acid, 1,12-dicarboxydodecane, fumaric acid, and maleic acid and (b) one of more of the following diols: ethylene glycol, polyethylene glycol, 1,2-propanediol, 1,3-propanediol, 1,2-propanediol, 1,2-butanediol, 1,3-butanediol, 1,4-butanediol, 1,6-hexanediol, diethylene glycol, and polypropylene glycol, and (c) optionally a small amount, i.e. 0.5-7.0 mole % of a polyol with a functionality greater than two such as glycerol, neopentyl glycol, and pentaerythritol.

Such polymers may include poly(butylenes succinate) homopolymer, poly(butylenes adipate) homopolymer, poly(butylenes adipate-succinate) copolymer, poly(ethylenesuccinate-adipate) copolymer, and poly(ethylene adipate) homopolymer.

Commercially available aliphatic polyesters include polylactide, polyglycolide, polylactide-co-glycolide, poly(L-lactide-co-trimethylene carbonate), poly(dioxanone), poly(butylene succinate), and poly(butylene adipate).

Especially useful aliphatic polyesters include those derived from semicrystalline polylactic acid. Polylactic acid (or polylactide) has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, polylactide polymers may be obtained having different stereochemistries and different physical properties, including crystallinity. The L,L- or D,D-lactide yields semicrystalline polylactide and are preferred, while the polylactide derived from the D,L-lactide is amorphous.

The polylactide preferably has a high enantiomeric ratio to maximize the intrinsic crystallinity of the polymer. The degree of crystallinity of a poly(lactic acid) is based on the regularity of the polymer backbone and the ability to line crystallize with other polymer chains. If relatively small amounts one enantiomer (such as D-) is copolymerized with the opposite enantiomer (such as L-) the polymer chain becomes irregularly shaped, and becomes less crystalline. For these reasons it is desirable to have a poly(lactic acid) that is at least 85% of one isomer, preferably at least 90%, and most preferably at least 95% in order to maximize the crystallinity.

An approximately equimolar blend of D-polylactide and L-polylactide is also useful in the present invention. This blend forms a unique crystal structure having a higher melting point (~210° C.) than does either the D-polylactide and L-polylactide alone (~190° C.), and has improved thermal stability. Reference may be made to H. Tsuji et. al., *Polymer*, 1999, 40 6699-6708.

Copolymers, including block and random copolymers, of poly(lactic acid) with other aliphatic polyesters may also be used. Useful co-monomers include glycolide, β-propiolactone, tetramethylglycolide, β-butyrolactone, γ-butyrolactone, pivalolactone, 2-hydroxybutyric acid, α-hydroxyisobutyric acid, α-hydroxyvaleric acid, α-hydroxyisovaleric acid, α-hydroxycaproic acid, α-hydroxyethylbutyric acid, α-hydroxyisocaproic acid, α-hydroxy-β-methylvaleric acid, α-hydroxyoctanoic acid, α-hydroxydecanoic acid, α-hydroxymyristic acid, and α-hydroxystearic acid.

Blends of poly(lactic acid) and one or more other aliphatic polyesters, or one or more other polymers may also be used in the present invention. Examples of useful blends include poly(lactic acid) and poly(vinyl alcohol), polyethylene glycol/polysuccinate, polyethylene oxide, polycaprolactone and polyglycolide.

In blends of aliphatic polyesters with a second amorphous or semicrystalline polymer, if the second polymer is present in relatively small amounts, the second polymer will generally form a discreet phase dispersed within the continuous phase of the aliphatic polyester. As the amount of the second polymer in the blend is increased, a composition range will be reached at which the second polymer can no longer be easily identified as the dispersed, or discrete phase. Further increase in the amount of second polymer in the blend will result in two co-continuous phases, then in a phase inversion wherein the second polymer becomes the continuous phase. Preferably, the aliphatic polyester component forms the continuous phase while the second component forms a discontinuous, or discrete, phase dispersed within the continuous phase of the first polymer, or both polymers form co-continuous phases. Where the second polymer is present in amounts sufficient to form a co-continuous phase, subsequent orientation and microfibrillation may result in a composite article comprising microfibers of both polymers.

Useful polylactides may be prepared as described in U.S. Pat. No. 6,111,060 (Gruber, et al.); U.S. Pat. No. 5,997,568 (Liu); U.S. Pat. No. 4,744,365 (Kaplan et al.); U.S. Pat. No. 5,475,063 (Kaplan et al.); WO 98/24951 (Tsai et al.); WO 00/12606 (Tsai et al.); WO 84/04311 (Lin); U.S. Pat. No. 6,117,928 (Hiltunen et al.); U.S. Pat. No. 5,883,199 (McCarthy et al.); WO 99/50345 (Kolstad et al.); WO 99/06456 (Wang et al.); WO 94/07949 (Gruber et al.); WO 96/22330 (Randall et al.); WO 98/50611 (Ryan et al.); U.S. Pat. No. 6,143,863 (Gruber et al.); U.S. Pat. No. 6,093,792 (Gross et al.); U.S. Pat. No. 6,075,118 (Wang et al.), and U.S. Pat. No. 5,952,433 (Wang et al.), the disclosure of each U.S. patent incorporated herein by reference. Reference may also be made to J. W. Leenslag, et al., *J. Appl. Polymer Science*, 1984, 29, 2829-2842, and H. R. Kricheldorf, *Chemosphere*, 2001, 43, 49-54.

In preparing microflakes or microfibrillated articles, the molecular weight of the polymer should be chosen so that the polymer is melt processible under the given processing conditions. The molecular weight for polylactide, for example, a may be from about 10,000 to 300,000 and is preferably from about 30,000 to 200,000. For polypropylene and polyethylene, the molecular weight may be from 5,000 to 500,000 and is preferably from about 190,000 to 300,000. By melt-processible it is meant that the polymeric materials are fluid or pumpable at the temperatures used to process the films and do not significantly degrade or gel at those temperatures. Generally, the $M_w$ of the polymers is above the entanglement molecular weight, as determined by a log-log plot of viscosity versus molecular weight ($M_n$). Above the entanglement molecular weight, the slope of the plot is about 3.4, whereas the slope of lower molecular weight polymers is 1.

In order to obtain the maximum physical properties and render the polymer film amenable to fibrillation, the polymer chains need to be oriented along two major axes (biaxial orientation). The degree of molecular orientation is generally defined by the draw ratio, that is, the ratio of the final length to the original length of the machine and transverse dimensions. The orientation may be effected by a combination of techniques including the steps of calendaring and length orienting.

The conditions for orientation are chosen such that the integrity of the film is maintained. Thus when stretching in the machine and/or transverse directions, the temperature is chosen such that substantial tearing or fragmentation of the continuous phase is avoided and film integrity is maintained. The film is particularly vulnerable to tearing, or even catastrophic failure if the temperature is too low, or the orientation ratio(s) is/are excessively high. Preferably, the orientation temperature is above the glass transition temperature of the continuous phase. Such temperature conditions permit maximum orientation in the X and Y directions without loss of film integrity, maximize voiding imparted to the film and consequently maximizing the ease with which the surface(s) may be microfibrillated. In the film small breakages or tears (microvoids) may occur when the deformation stress due to orientation exceeds the rate of disentangling of the polymer molecules. See, for example, Roger S. Porter and Li-Hui Wang, Journal of Macromolecular Science-Rev. Macromol. Chem. Phys., C35(1), 63-115 (1995).

A general method has been developed for producing highly oriented, microfibrillated, thermoplastic polymeric films. The polymer film is formed via typical melt extrusion using a T or "coat hanger die" and quenched using a multiple roll take up stack. The temperature of the rolls is maintained around 21° C., such that the extruded film is rapidly quenched and crystallization is minimized, i.e. the film is substantially amorphous. The film or extruded profile is then stretched using a two-stage process. In the first stage, the film is stretched above the glass transition temperature to a sufficient draw ratio at a relatively high strain rate such that the film microvoids, but does not fail catastrophically. The film may be stretched by a variety of methods including but not limited to roll drawing (calendering), length orienting using hot rolls, zone drawing, or hot drawing in a liquid media. Length orienting has been used extensively in traditional film processing often in the first step of a sequential biaxial orientation process. If a voiding agent is used, extensive voiding can be realized as the particle de-bonds from the thermoplastic polymer. Also, voiding agents may be added to the polymer melt to improve the microfibrillation efficiency, such as non-compatible polymers, silica, calcium carbonate or micaceous materials or to impart a desired property to the microfibers, such as antistats or colorants. Typically, a draw ratio of 4:1-6:1 can be achieved in the first stage dependent on the polymer that is used. Processes for biaxially orienting films and microfibrillating such films for the preparation of microfibrillated articles is described in U.S. Pat. No. 6,331,433, which patent is also incorporated herein by reference.

The second stage stretching process is performed at a higher draw temperature below the melting point of the polymer than the temperature of the first stage. In this stage, the film is further drawn to a high ratio and a microfibrillar structure is observed. The increase in molecular orientation can be measured using X-ray scattering and changes in crystallinity by DSC. Usually in the second stage, the crystallinity increases significantly due to the higher orientation and temperature imposed in the process. The preferred method of stretching is length orientation using hot rolls running at different speeds. The final voided or microvoided film has a silvery appearance and can be easily split in the direction of the drawing (machine direction). Additional drawing stages allow the film to be further oriented but are not necessary.

For example, with polylactide, the films may be stretched greater than 6 times its length. In one embodiment, the total draw ratio is greater than 6:1 and preferably in the range of 9:1 to about 18:1 for polylactide. "Total draw ratio" is the ratio of the final area of the film to the initial area of the film.

Further, crystallinity may be developed in a melt-processed film comprising an aliphatic polyester, for example, and void-initiating component. It is preferred that the aliphatic polyester film be substantially amorphous and crystallinity increased by an optimal combination of subsequent processing such as calendering, stretching, recrystallization and annealing following recrystallization. It is believed that maximizing the crystallinity of the film will increase microfibrillation efficiency. Normally, the aliphatic polyester is cast as a substantially amorphous film and then crystallinity increased by strain induced crystallization. Specific useful combinations of aliphatic polyester/void initiating component blends include, for example, polylactide and inorganics particles such as $CaCO_3$, and polylactide and polypropylene.

A film or foam may be biaxially oriented by stretching in mutually perpendicular directions at a temperature above the glass transition temperature of the thermoplastic polymer phase. Generally, the film is stretched in one direction first and then in a second direction perpendicular to the first. However, stretching may be effected in both directions simultaneously if desired. In a typical process, the film is stretched first in the direction of extrusion over a set of rotating rollers or between two pairs of nip rollers and is then stretched in the direction transverse thereto by means of a tenter apparatus. Films may be stretched in each direction up to 2 to 10 times their original dimension in the direction of stretching.

It is preferred to restrict the stretching in the transverse direction to less than 2× for some polymeric materials. It has been found that the ability to microfibrillate the films is compromised if the film is oriented in a first direction (e.g. in the machine direction) and subsequently oriented in the perpendicular direction more than 2×. It is preferred that the films be oriented uniaxially in a first direction to the desired draw ratio, and then in the perpendicular direction less than 2×. It will be understood, however, that in the uniaxial orientation, the film may be restrained from shrinking in the lateral direction by means of a tenter apparatus, and such restraint does impose a small degree of biaxial orientation to the film. Such small degrees of biaxial orientation may enhance subsequent microfibrillation.

After the film has been stretched it may be further processed. For example, the film may be annealed or heat-set by subjecting the film to a temperature sufficient to further crystallize the thermoplastic polymer component while restraining the film against retraction in both directions of stretching.

Upon orientation, voids may be imparted to a film of an immiscible blend. As the film is stretched, the two components separate due to the immiscibility of the two components and poor adhesion between the two phases. When the film comprise a continuous phase and a discontinuous phase, the discontinuous phase serves to initiate voids which remain as substantially discrete, discontinuous voids in the matrix of the continuous phase. When two continuous phases are present, the voids that form are substantially continuous throughout the polymer film. Typical voids have major dimensions X and Y, proportional to the degree of orientation in the machine and transverse direction respectively. A minor dimension Z, normal to the plane of the film, remains substantially the same as the cross-sectional dimension of the discrete phase (void initiating component) prior to orientation. Voids arise due to poor stress transfer between the phases of the immiscible blend. It is believed that low molecular attractive forces between the blend components are responsible for immiscible phase behavior; low interfacial tension results in void formation when the films are stressed by orientation or stretching.

The voids are relatively planar in shape, irregular in size and lack distinct boundaries. Voids are generally coplanar with the film, with major axes in the machine (X) and transverse (Y) directions (directions of orientation). The size of the voids is variable and proportional to the size of the discrete phase and degree of orientation. Films having relatively large domains of discrete phase and/or relatively high degrees of orientation will produce relatively large voids. Films having a high proportion of discrete phases will generally produce films having a relatively high void content on orientation. Void size, distribution and amount in the film matrix may be determined by techniques such as small angle x-ray scattering (SAXS), confocal microscopy, scanning electron microscopy (SEM) or density measurement. Additionally, visual inspection of a film may reveal enhanced opacity or a silvery appearance due to significant void content.

Foams and films formed from a polymer mixture containing a minor immiscible component for generating voids are important for forming schistose microfibrillated articles. Typically, the foam or film oriented via a continuous process may yield up to about a 6:1 draw ratio in the machine direction, and up to about a 10:1 draw ratio in the transverse direction. In a batch process oriented film or foam, a draw ratio of up to about 15:1 in both the machine and transverse directions may be achieved.

Generally, greater void content enhances the subsequent microfibrillation, and subsequently, using the process of this invention, for uniaxially oriented films, the greater the yield of fibers. Preferably, when preparing an article having at least one microfibrillated surface, the polymer film should have a void content in excess of 5%, more preferably in excess of 10%, as measured by density; i.e., the change in density divided by the initial density; $(\delta_{initial}-\delta_{final})/\delta_{initial}$. Unexpectedly, it has been found that voids may be imparted to the two component (first polymer and void initiating) polymer films under conditions far less severe than those necessary to impart microvoids to microvoided films previously described. It is believed that the immiscible blend, with limited solubility of the two phases and a free energy of mixing greater than zero, facilitates the formation of the voids necessary for subsequent microfibrillation. Furthermore, voiding is aided by lower orientation temperatures utilized in the first orientation stage. Microvoided films may be distinguished from other voided films or articles, such as microporous films or foamed articles in that the microvoids are generally non-cellular, relatively planar and have major axes in the machine direction (direction of orientation) of the film. The microvoids do not generally interconnect, but adjacent microvoids may intersect.

Too low of an orientation temperature may result in a film with an uneven appearance. Increasing the first orientation temperature may reduce the uneven stretching, giving the stretched film a more uniform appearance. The first orientation temperature also affects the amount of voiding that occurs during orientation. In the temperature range in which voiding occurs, the lower the orientation temperature, generally the greater the amount of voiding that occurs during orientation. As the first orientation temperature is raised, the degree of voiding decreases to the point of elimination. Electron micrographs of samples show that, at temperatures at which no voiding occurs, the discrete phases domains often deform during stretching. This is in contrast to highly voided oriented samples; electron micrographs of highly voided samples show that the discrete phase domains retain their approximately shape during orientation. A second orientation, in the same direction, or in a direction perpendicular to the first orientation may be desired. The temperature of such second orientation is generally similar to or higher than the temperature of the first orientation.

Visual inspection of a film may reveal enhanced opacity or a silvery appearance due to significant microvoid content that can serve as an empirical test of the suitability of an oriented film for the production of a microfibrillated surface. In contrast, film surfaces lacking significant microvoids have a transparent appearance. It has been found that an oriented film lacking in significant amount of microvoids is not readily microfibrillated, even though the film may be split longitudinally, as is characteristic of highly oriented polymer films having a fibrous morphology.

The thickness of the film will be chosen according to the desired end use and can be achieved by control of the process conditions. Cast films will typically have thicknesses of less than 100 mils (2.5 mm), and preferably between 20 and 70 mils (0.8 to 1.8 mm). However, depending on the characteristics desired for the resultant article, they may be cast at thicknesses outside of this range. Cast films and blown films may also be used to produce microfibrillated articles. The final thickness of the film will be determined in part by the casting thickness, and the degree of orientation. For most uses, the final thickness of the film prior to microfibrillation will be 1 to 20 mils (0.025 to 0.5 mm), preferably 3 to 10 mils (0.075 to 0.25 mm). Further, the processes described herein can also be advantageously used on films that have been simultaneously biaxially stretched. Such stretching can be accomplished, for example, by the methods and apparatus disclosed in U.S. Pat. No. 4,330,499 (Aufsess et al.) and U.S. Pat. No. 4,595,738 (Hufnagel et al.), and more preferably by the methods and tenter apparatus disclosed in U.S. Pat. No. 4,675,582 (Hommes et al.); U.S. Pat. No. 4,825,111 (Hommes et al.); U.S. Pat. No. 4,853,602 (Hommes et al.); U.S. Pat. No. 5,036,262 (Schonbach); U.S. Pat. No. 5,051,225 (Hommes et al.); and U.S. Pat. No. 5,072,493 (Hommes et al.), the disclosures of which are herein incorporated by reference.

Depending on the thickness of the extruded article, the temperature and the means by which the film is quenched, the morphology of the thermoplastic substrate may not be the same across the thickness of the article, i.e., the morphology of the two surfaces and/or the morphology of the surfaces and the matrix may be different. Small differences in morphology do not normally prevent the formation of a microfibrillated surface on either major surface on the film, but if microfibrillated surfaces are desired on both surfaces of the article, it is preferred that casting conditions be carefully controlled to ensure a relatively uniform amorphous morphology across the thickness of the article. The polymeric matrix used in this invention comprises microflakes and/or microfibrillated articles having average lengths of 20 micrometers or less.

Microfibrillated materials can also include biaxially oriented and foamed polymers, preferably thermoplastic polymers. The foam may be made using extrusion processing by adding one or more polymers and gas or supercritical fluid to a twin screw or single screw extruder. Thereafter, the foamed polymer is biaxially oriented. Exemplary high melt strength foamable thermoplastic polymers include polypropylenes that may consist of propylene homopolymers or may comprise a copolymer having 50 weight percent or more propylene monomer content. The foamable polypropylenes may comprise a mixture or blend of propylene homopolymers or copolymers with a homo- or copolymer other than propylene homo- or copolymers. Further microfibrillated polypropylene containing materials and articles are described in U.S. Pat. No. 6,692,823 (Kody et al.), U.S. Pat. No. 6,468,451 (Perez et al.), and U.S. Pat. No. 6,890,649 (Hobbs et al).

In one embodiment, the microfibers and/or microfibrillated articles may be prepared from microvoided films using the processes described in U.S. Pat. No. 6,110,588, the entire disclosure of which is incorporated by reference. The disclosed microvoided films are derived from a highly oriented, semicrystalline, melt processed film having a strain induced crystallinity. Strain induced crystallinity is the crystallinity that may be obtained by an optimal combination of subsequent processing such as calendering, annealing, stretching and recrystallization.

The oriented thermoplastic film may be microfibrillated by imparting sufficient fluid energy to the surface to release the microfibers from the polymer matrix. In a microfibrillation process, relatively greater amounts of energy are imparted to the film surface to release microflakes, relative to that of a conventional mechanical fibrillation process. Microflakes are obtained from a biaxially oriented film precursor substrate. After microfibrillation, the majority of the material's surface comprises schistose surface structures. These structures have an average thickness of 1 to 20 micrometers, preferably less than 5 micrometers, an average width of from 1 to 200 micrometers, preferably from about 5 to about 30 micrometers and an average length of 1 to 20 micrometers, preferably 1 to 3 micrometers. The schistose structures can typically exhibit surface areas greater than 0.5 $m^2$/gram, preferably greater than 0.7 $m^2$/gram, as measured using an Autosorb-6 Physisorption Analyzer (Quantachrome Instruments, Boynton Beach, Fla.) with nitrogen as the absorbate. Scanning electron microscopy reveals that the microflakes used in the present invention are generally parallel to one another, and are shaped like a plate or a plate-like ribbon where the length scale of two of the microflake dimensions (width and length) is at least 10 times, preferably at least 20 times, that of the microflake's third dimension-thickness. An aspect ratio of the schistose surface of the microflakes may range from 1:1 to 1:20, and can depend on how balanced the orientation of the film or foam is. A more unbalanced stretch leads to a more tape-like microflake. Further, the flakes can be connected to one another, and tend to be continuous in a width or length direction. Dimensions can be measured using a scanning electron microscope. The surface area enhances bonding in matrices such as concrete and thermoset plastics, as well as provide greater surface area for enhanced biodegradability, where desired.

Optionally, prior to microfibrillation, the film may be subjected to a macrofibrillation step by conventional mechanical means to produce macroscopic flakes from the biaxially oriented film. The conventional means of mechanical fibrillation uses a rotating drum or roller having cutting elements such as needles or teeth in contact with the moving film. The teeth may fully or partially penetrate the surface of the film to impart a macrofibrillated surface thereto. Other similar macrofibrillating treatments are known and include such mechanical actions as twisting, brushing (as with a porcupine roller), rubbing, for example with leather pads, and flexing. The flakes obtained by such conventional macrofibrillation processes are macroscopic in size, generally several hundreds of micrometers in cross section.

One method of microfibrillating the surface of the film is by means of fluid jets. In this process one or more jets of a fine fluid stream impact the surface of the thermoplastic polymer film, which may be supported by a screen or moving belt, thereby releasing the microflakes from the polymer matrix. One or both surfaces of the film may be microfibrillated. The degree of microfibrillation is dependent on the exposure time of the film to the fluid jet, the pressure of the fluid jet, the cross-sectional area of the fluid jet, the fluid contact angle, the polymer properties and, to a lesser extent, the fluid temperature. Different types and sizes of screens can be used to support the film.

Any type of liquid or gaseous fluid may be used. Liquid fluids may include water or organic solvents such as ethanol or methanol. Suitable gases such as nitrogen, air or carbon dioxide may be used, as well as mixtures of liquids and gases. Any such fluid is preferably non-swelling (i.e., is not absorbed by the polymer matrix), which would reduce the orientation and degree of crystallinity of the microflakes. For imparting a charge during micro fibrillation, the preferred fluid is water and is most preferably deionized or distilled water substantially free of any contaminants such as salts or minerals that could dissipate the electrostatic charge. The fluid temperature may be elevated, although suitable results may be obtained using ambient temperature fluids. The pressure of the fluid should be sufficient to impart some degree of microfibrillation to at least a portion of the film, and suitable conditions can vary widely depending on the fluid, the nature of the polymer, including the composition and morphology, configuration of the fluid jet, angle of impact and temperature. Generally, less severe conditions are needed to microfibrillate the voided films and voided foams when compared to the microvoided films.

Typically, the fluid is water at room temperature and at pressures of greater than 6800 kPa (1000 psi), preferably greater than 10,300 kPa (1500 psi) although lower pressure and longer exposure times may be used. Such fluid will generally impart a minimum of 10 watts or 20 W/cm$^2$ based on calculations assuming incompressibility of the fluid, a smooth surface and no losses due to friction.

The configuration of the fluid jets, i.e., the cross-sectional shape, may be nominally round, but other shapes may be employed as well. The jet or jets may comprise a slot which traverses a section or which traverses the width of the film. The jet(s) may be stationary, while the film is conveyed relative to the jet(s), the jet(s) may move relative to a stationary film, or both the film and jet may move relative to each other. For example, the film may be conveyed in the machine (longitudinal) direction by means of feed rollers while the jets move transverse to the web. Preferably, a plurality of jets is employed, while the film is conveyed through the microfibrillation chamber by means of rollers, while the film is supported by a screen or scrim, which allows the fluid to drain from the microfibrillated surface. The film may be microfibrillated in a single pass, or alternatively the film may be microfibrillated using multiple passes past the jets.

The jet(s) may be configured such that all or part of the film surface is microfibrillated. Alternatively, the jets may be configured so that only selected areas of the film are microfibrillated. Certain areas of the film may also be masked, using conventional masking agents to leave selected areas free from microfibrillation. Likewise, the process may be conducted so that the microfibrillated surface penetrates only partially, or fully through the thickness of the starting film. If it is desired that the microfibrillated surface extend through the thickness of the film, conditions may be selected so that the integrity of the article is maintained and the film is not severed into individual yarns or flakes. A screen or mesh may be used to impart a pattern to the surface of the microfibrillated article.

A hydroentangling machine, for example, can be employed to microfibrillate one or both surfaces by exposing the fibrous material to the fluid jets. Hydroentangling machines are generally used to enhance the bulkiness of microfibers or yarns by using high-velocity water jets to wrap or knot individual microfibers in a web bonding process, also referred to as jet lacing or spunlacing. Alternatively a pressure water jet, with a swirling or oscillating head, may be used, which allows manual control of the impingement of the fluid jet.

With the use of fluid jets, the degree of microfibrillation can be controlled to provide a low degree or high degree of microfibrillation. A low degree of microfibrillation may be desired to enhance the surface area by partially exposing a minimum amount of microflakes at the surface and thereby imparting a fibrous texture to the surface of the film. The enhanced surface area consequently enhances the bondability of the surface. Such articles are useful, for example as substrates for abrasive coatings and as receptive surfaces for printing, as hook and loop fasteners, as interlayer adhesives and as tape backings. Conversely, a high degree of microfibrillation may be required to impart a highly schistose texture to the surface to provide cloth-like films, insulating articles, filter articles or to provide for the subsequent harvesting of individual microflakes (i.e., removal of the microflakes) from the precursor polymer film matrix.

In another embodiment, the microfibrillation may be conducted by immersing the sample in a high-energy cavitating medium. One method of achieving this cavitation is by applying ultrasonic waves to the fluid. The rate of microfibrillation is dependent on the cavitation intensity. Ultrasonic systems can range from low acoustic amplitude, low energy ultrasonic cleaner baths, to focused low amplitude systems up to high amplitude, high intensity acoustic probe systems.

One method, which comprises the application of ultrasonic energy, involves using a probe system in a liquid medium in which the fibrous film is immersed. The horn (probe) should be at least partially immersed in the liquid. For a probe system, the oriented film is exposed to ultrasonic vibration by positioning it between the oscillating horn and a perforated metal or screen mesh (other methods of positioning are also possible), in the medium. Advantageously, both major surfaces of the film are microfibrillated when using ultrasound. The depth of microfibrillation in the fibrous material is dependent on the intensity of cavitation, amount of time that it spends in the cavitating medium and the properties of the fibrous material. The intensity of cavitation is a factor of many variables such as the applied amplitude and frequency of vibration, the liquid properties, fluid temperature and applied pressure and location in the cavitating medium. The intensity (power per unit area) is typically highest beneath the horn, but this may be affected by focusing of the sonic waves.

The method comprises positioning the film between the ultrasonic horn and a film support in a cavitation medium (typically water) held in a tank. The support serves to restrain the film from moving away from the horn due to the extreme cavitation that takes place in this region. The film can be supported by various means, such as a screen mesh, a rotating device that may be perforated or by adjustment of tensioning rollers that feed the film to the ultrasonic bath. Film tension against the horn can be alternatively used, but correct positioning provides better fibrillation efficiency. The distance between the opposing faces of the film and the horn and the screen is generally less than about 5 mm (0.2 inches). The distance from the film to the bottom of the tank can be adjusted to create a standing wave that can maximize cavitation power on the film, or alternatively other focusing techniques can be used. Other horn to film distances can also be used. The best results typically occur when the film is positioned near the horn or at ¼ wavelength distances from the horn, however this is dependent on factors such as the shape of the fluid container and radiating surface used. Generally positioning the sample near the horn, or the first or second ¼ wavelength distance is preferred.

The ultrasonic pressure amplitude can be represented as:

$$P_o = 2\pi B/\lambda = (2\pi/\lambda)\rho c^2 y_{max}$$

The intensity can be represented as:

$$I = (Po)^2/2\rho c$$

where $P_o$=maximum (peak) acoustic pressure amplitude
$I$=acoustic intensity
$B$=bulk modulus of the medium
$\lambda$=wavelength in the medium
$y_{max}$=peak acoustic amplitude
$\rho$=density of the medium, and
$c$=speed of the wave in the medium.

Ultrasonic cleaner bath systems typically can range from 1 to 10 watt/cm$^2$ while horn (probe) systems can reach 300 to 1000 watt/cm$^2$ or more. Generally, the power density levels (power per unit area, or intensity) for these systems may be determined by the power delivered divided by the surface area of the radiating surface. However, the actual intensity may be somewhat lower due to wave attenuation in the fluid. Conditions are chosen so as to provide acoustic cavitation. In general, higher amplitudes and/or applied pressures provide more cavitation in the medium. Generally, the higher the cavitation intensity, the faster the rate of microflake production, yielding finer (smaller diameter) microflakes. While not wishing to be bound by theory, it is believed that high-pressure shock waves are produced by the collapse of the incipient cavitation bubbles, which impacts the film resulting in micro fibrillation.

The ultrasonic oscillation frequency is usually 20 to 500 kHz, preferably 20-200 kHz and more preferably 20-100 kHz. However, sonic frequencies can also be utilized without departing from the scope of this invention. The power density (power per unit area, or intensity) can range from 1 W/cm$^2$ to 1 kW/cm$^2$ or higher. In the present process, it is preferred that the power density be 10 watt/cm$^2$ or more, and preferably 50 watt/cm$^2$ or more.

The gap between the film and the horn can be, but it is not limited to, 0.001 to 3.0 inches (0.03 to 76 mm), preferably 0.005 to 0.05 inches (0.13 to 1.3 mm). The temperature can range from 5 to 150° C., preferably 10 to 100° C., and more preferably from 20 to 60° C. A surfactant or other additive can be added to the cavitation medium or incorporated within the fibrous film. The treatment time depends on the initial morphology of the sample, film thickness and the cavitation intensity. This time can range from 1 millisecond to one hour, preferably from 1/10 of a second to 15 minutes and most preferably from 1/2 second to 5 minutes.

Further, in either microfibrillation process, the degree or depth of microfibrillation can be controlled. Microfibrillated articles may be prepared in which the depth of microfibrillation (i.e. the thickness of the microfibrillated layer) is as little as 10 micrometers, but may be 50 micrometers or greater, 100 micrometers or greater, up to the thickness of a completely microfibrillated film. A low degree of microfibrillation may be desired to enhance the surface area by partially exposing a minimum amount of microflakes at the surface and thereby imparting a fibrous texture to the surface of the film. Conversely, a high degree of microfibrillation may be required to impart a highly fibrous schistose texture to the surface to provide cloth-like films, insulating articles and filter articles.

In either microfibrillation process, most of the microflakes stay attached to the precursor film due to incomplete release from the polymer matrix. Advantageously, the microfibrillated article, having microflakes secured to a film, provides a convenient and safe means of handling, storing and transporting the microflakes. For many applications, it is desirable to retain the microflakes secured to the web as described in U.S. Pat. No. 6,645,618 (Hobbs et al.) and U.S. Pat. No. 6,890,649 (Hobbs et al.), which are herein incorporated by reference.

Optionally, the microflakes may be harvested from the surface of the film by mechanical means such as with a porcupine roll, scraping and the like. Harvested microflakes generally retain their bulkiness (loft) due to the high modulus of the individual microflakes. If necessary, loft may be improved by conventional means, such as those used to enhance the loft of blown microflakes, for example by the addition of staple fibers.

The microfibrillated article and microflakes used in this invention present fiber dimensions that are important for cell growth. The plate-like shape of the microflakes favors cell attachment, where the high surface area should allow for faster degradation with aliphatic polyesters. The subcellular flake size of the microflakes has excellent mechanical strength and drapeability, and can be produced in a continuous method.

As described in this invention, tissue cells require a solid substratum upon which they can move and extend only short protrusions into a liquid medium. In the human body, collagen, other extracellular fibers, or the surfaces of other cells would serve as the solid substratum. Also, cells can readily crawl onto glass and other common tissue culture substrates. The motility of tissue cells can be strongly influenced by the adhesiveness and physical shape of the substrate, such as microflakes, where cells accumulate on regions of greater adhesiveness, and move up adhesion gradients. These cells flatten in proportion to the adhesiveness of their substrate. Cells may orient along the microflakes and curved surfaces spreading and moving preferentially along the direction of minimal local curvature. As cells grow, contact with another cell may inhibit one another's locomotion. However, white blood cells and cancerous cells are relatively insensitive to inhibition and their invasive capabilities.

Tissue-derived cells, such as mammalian cells, can be cultured in a cell culture medium as a synthetic environment. A complete growth medium is defined as containing nutrients, and is referred to as a substance on or in which microorganisms or cells can be grown. The cell culture medium contains salts, carbohydrates, vitamins, amino acids, and metabolic precursors. Additionally, this medium may be supplemented with sera, growth factors, trace elements, hormones, and antibiotics, which is referred to as the complete growth medium. The medium bathes the cells attached to the surface of the vessel, where the cultures can be grown, and subsequently subcultured. Without the addition of hormones or growth factors, some cell lines would be incapable of growth. The required components for a medium vary among the cell lines, and account for the comprehensive listing of cell cultures mediums. Some example mediums include Eagle's Minimum Essential Medium, Dulbecco's Modified Eagle's Medium, and Iscove's Modified Dulbecco's Medium. Cell culture mediums are specific to their respective cell lines. A listing of cell culture mediums is available from Invitrogen Corporation (Carlsbad, Calif.).

The cell culture medium is beneficial to cell growth and development. In addition to the nutrients listed, the medium helps maintain the pH and osmolality in a culture system. Typical cell culture media for most vertebrate cells is within 260 to 320 mOsm/kg with more established cell lines tolerating a larger variation in osmotic pressure. This applies to either prokaryotic or eukaryotic cells, even though in practice cell culture has come to refer to the culturing of cells derived from multicellular eukaryotes, especially animal cells. Culture conditions (growth media, pH and temperature) vary widely for each cell type and variation of conditions for a particular cell type can result in different phenotypes being expressed. Reference to cell culturing can be found in Sanford, K. K., The growth in vitro of single isolated tissue cells, *J. Natl. Cancer Inst.* 1948, 9, 229-246; Freshney, R. I., *Culture of Animal Cells: A Manual of Basic Technique*, 4$^{th}$ Ed. New York: Wiley Liss, 2000; Jacoby, W. B., Pasten, I. H., eds., "Monolayer culture techniques in Methods in Enzymology", *Cell Culture,* 1979, 58, New York, Academic Press; and Wickert, P. D. et. al., WO 00/53721, Sep. 14, 2000.

Typically, the vessel for culturing cells provides a contamination barrier to protect the cultures from the external environment while maintaining the proper internal environment. Glass and plastic (ie. polystyrene) are most commonly used for cell growth. In this invention, the microflakes or microfibrillated article (having a schistose surface) may be dispersed in a cell culture medium within a vessel for culturing cells. The cells are inoculated onto the surface of the microfibrillated article, and provided an environment to grow. Additionally, the microfibrillated article may comprise a matrix for a multi-well plate device for culturing cells.

A cell line is grown and maintained under appropriate conditions with a culture of cells that grow and replicate continuously. All cell lines originate from cell cultures with a limited lifetime, but occasionally some cells keep on multiplying due to genetic instability. These cells can be cultured indefinitely. Cell lines can be found at American Type Culture Collection (ATCC) BioProducts (Manassas, Va.).

Cells can be cultured for a longer time if they are split regularly, where the growth medium is then replaced and the cells are diluted (after first detaching them with trypsin from the support) is referred to as subculturing. The key to success in culturing cells is to mimic the environment, as described in the article of this invention, in which they found themselves before being transplanted to an artificial environment. Secondly, the cultured cells may be subcultured frequently. When the cells are about 70 to 90% confluent, it may be necessary to subculture them. The subcultivation of cell monolayers involves the breakage of both intercellular and cell-to-cell surface connections. Typically, the protein attachment bonds are digested with trypsin. After cell dissociation and dispersion into a single cell suspension, the cells are further diluted or split and transferred into fresh culture vessels for continued reattachment, growth and division. A confluent cell layer is where the cells touch each other to form a monolayer. Many culture mediums are available for the cell line of interest to best replicate an artificial environment for successful cell growth.

Mammalian cells are important for the evaluation of wound healing, since they ultimately produce fibrous tissue rather than new cells. Mouse and human diploid fibroblasts, for example, may be added to a cell culture medium, incubated at an elevated temperature where the medium is changed every 3-5 days, and subcultured. The monolayer of cells, from where the cells were removed, will continue to be incubated. Cell density is also important for cell growth where the cells need an unceasing supply of energy and materials to maintain them. The complete cell growth medium within which the microfibrillated article is dispersed supports the viability of the cells.

A method of culturing cells is described. In this invention, a matrix of biaxially oriented, thermoplastic substrate having a schistose surface comprising microflakes are dispersed in a cell culture medium, where the matrix is inoculated with cells. The matrix acts as an extracellular matrix. It is important for cells in tissue scaffolding to have a polymeric material that acts as an extracellular matrix allowing the cells to grow into it, attach, and proliferate. The small, flat microflakes of this matrix provide a substrate for cell growth similar to living tissue where opportunities exist for wound healing and tissue scaffolding applications. The microflakes support cell proliferation, and cell attachment. These properties may be observed when the microflakes provide a large amount of open space, stiffness, and a flat morphology. The geometry of the biaxially oriented, thermoplastic substrate having a schistose surface comprising microflakes may be important for faster biodegradation of some polymeric materials than found with a round fiber of similar dimensions as a result of its greater surface area. Scanning electron micrographs show that fiber size, geometry and interstitial spacing have an effect on the density of cells on the matrix, the morphology of the cells, and the amount of cell spreading. Smaller flat flakes of the microfibrillated article appear to have a higher density of cells with more spreading and cell attachment as shown in FIG. 1 of Example 3.

Further, the three-dimensional structure of the microfibrillated article provides stiffness and resistance to snag and collapse. The extracellular matrix directs the way cells interact with each other and brings out specific cellular functions. The synthetic scaffold may comprise biodegradable and biocompatible materials, such as aliphatic polyesters. The highly porous nature of the article, due to interstitial spaces between the microflakes of the microfibrillated article, allows for cell penetration as well as polymer degradation. In wound healing, especially in primary and secondary wounds, epithelialization occurs when the epithelial cells migrate and proliferate over the wound surface. A biodegradable material may guide these cells to migrate across the surface and facilitate wound healing.

Polylactide, polyglycolide, and copolymers thereof, along with other aliphatic polyesters known may be used in this invention. The comonomer content of these polymers can be used to control the degradation times and rates. Various surface treatments such as plasma treatment, corona treatment and the adsorption of a polymer with a specified peptide sequence may be used. Nutrients and growth factors may also be applied to a surface. The microfibrillated surface may be subsequently seeded and cultured to create a functional tissue analogous to an in vivo tissue. The extracellular matrix may further be used as a generic cell culture media for large scale cultures as a result of the substantial fiber strength.

The cultured cells need an environment in which they can adhere, proliferate and differentiate on a matrix, and further develop new tissue. The morphology of the microfibrillated article, when used as a scaffold provides for the steps for cell survival. In vitro and in vivo applications with a synthetic extracellular matrix may allow for a three dimensional arrangement of cells. The cells may thrive in this environment in which they may behave and grow analogous to cells in the human body.

Further, this invention provides for an article for a cell growth matrix, wherein the microflakes that may be inoculated with cells are dispersed within a cell culture medium. In vertebrates, almost all of the cells are in contact with a complex network of extracellular macromolecules, or an extracellular matrix. The main components are collagens and proteoglycans, where the collagen in fibrillar form has a diameter of 0.01 to 1 micrometers, depending on the tissue and the organism. A difficulty encountered in conventional culture techniques is dedifferentiation. The cells are normally separated from their tissue specific extracellular matrix followed by suspension in a growth medium where they adhere to the bottom of a culture dish to form a confluent monolayer. The dedifferentiated cells may lose their morphology as well as their biochemical and functional properties resulting in completely different behavior compared to their original tissue environment. In order for the cells to proliferate and differentiation, cellular attachment to a microfibrillated article is important. The matrix surface may be modified with a peptide sequence to promote recognition and rapid adhesion. The three-dimensional matrix of the biaxially oriented, thermoplastic substrate comprising microflakes allows for the diffusion of nutrients in and cellular waste out of the matrix. The use of fibroblasts through cell attachment and proliferation allow for aliphatic polyester microflakes to partner in the formation of a three-dimensional artificial tissue. Flake size, shape, surface energy, and bioabsorptivity render these fibers useful as an extracellular matrix or for in vivo applications.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
| --- | --- |
| Microflake-1 | Microfibrillated biaxially oriented article prepared as described in U.S. Pat. No. 6,468,451 Example 3 except that a 70/30 by weight blend of polylactic acid/polycaprolactone was used in place of the PP/elastomer and the foam blend was biaxially oriented in a 4 × 4 ratio as described in U.S. Pat. No. 6,331,343. The polylactic acid had a density of 1.25 g/cc and a $T_g$ of 58° C. The polycaprolactone was TONE 767 commercially available from DOW Plastics, Micland, MI. |
| Microflake-2 | PLA low-density foam-biaxially oriented 2.8 × 2.8 and hydroentangled at 2000 psi. Microfibrillated biaxially oriented polylactic acid article prepared as described in U.S. Pat. No. 6,468,451 Example 3 except that polylactic acid was used in place of the PP/elastomer and the foam blend was biaxially oriented in a 2.8 × 2.8 ratio as described in U.S. Pat. No. 6,331,343. The polylactic acid had a density of 1.25 g/cc and a Tg of 58° C.. |
| Microflake-3 | Microfibrillated polypropylene-polyethylene terephthalate article prepared as described in U.S. Pat. No. 6,331,343 Example 3 except that PET (extrusion grade polyethylene terephthalate from 3M Company, St. Paul, MN as described in U.S. Pat. No. 6,331,343 Example 6) was used in place of PBT. |

Microfibrillated polymeric materials such as poly(lactic acid), poly(carbonate), polypropylene, and their copolymers and blends have been studied with cultured cells to evaluate their effectiveness in cell growth. These precursor film materials have been oriented and microfibrillated to achieve a three dimensional matrix having a schistose surface. It is desired in tissue engineering to create a structure that can function well enough to replace or become a part of an organ or tissue that is not functioning properly in a living system. This provides a more efficient and reduced cost method for replacing and restoring a defective tissue or organ. In tissue engineering, the source of the tissue would be of the subject's own cells, thus avoiding rejection by the body's own immune system. In most tissue engineering cases, matrices are used to deliver cells to a desired site, define a space for a tissue, and guide the process for tissue development. Most of these cells are anchorage dependent and need an adhesion-like substrate in which to adhere. Ideally, the matrix should act like the body's own natural extracellular matrix (ECM). The ECM brings out specific cellular functions and directs the way cells interact with each other. The synthetic thermoplastic tissue scaffold used in this invention provides for this function.

Thermoplastic polymeric materials provide good examples of synthetic scaffolds. However, the polymeric materials are preferred to be biocompatible. Common synthetic polymeric materials include poly(lactic acid) (PLA), and poly(ε-caprolactone) PCL, which are biodegradable. These materials may be extruded, and microfibrillated resulting in a highly schostose surface of microflakes with an average effective length of less than 20 micrometers, and a width of less than 200 micrometers.

Examples 1-3 and Comparative Example C1

For Examples 1-3, Microflakes 1-3 were used. For Comparative Example C1 no microfibrillated article was used, rather the membrane present in the Transwell plates was left in. The procedure for cell growth and testing is given in the multi-step process below.

Step 1: Sterilization

Each of the microfibrillated articles Microflakes 1-3 were sterilized using ethylene oxide by exposing the samples to ethylene oxide gas at 37 degrees Celsius (cold cycle) for 4-4.5 hours and then aerated for 2-3 days at 37 degrees Celsius.

Step 2: Cell Culture Preparation

The first step in starting the cell culture was to prepare the medium in which they would grow. One packet of powdered Basal Medium Eagle (BME) was added to 1,000 milliliters of sterile water and stirred until dissolved. Next, 0.35 milligram of sodium bicarbonate was measured and dissolved into the BME solution and the pH of the solution was measured. The desired pH was around 7.4. The solution was heated to 37° C. in a water bath. When the solution reached 37° C., 5 milliliters of the antibiotic penicillin and 50 milliliters of fetal bovine serum (FBS) were added (they were also heated to 37° C.). The bottles containing the final solutions were marked "complete" to indicate that they contained everything they needed.

The cells used were L929 mouse fibroblasts. 1 milliliter of the mouse fibroblasts was added to 3 milliliters of the completed medium prepared above and was broken apart by manually titrating with a 5 milliliter pipette. 4 milliliters of suspended cells in the completed medium was transferred to two plastic 200 milliliter culture flasks (2 milliliters in each). The two flasks were placed in an incubator set at 37° C. Four days later, the medium was changed by pouring off the old medium of both flasks and pipetting 30 milliliters of Dulbecco's Modified Eagle's Medium (DMEM) (37° C.) into each culture flask. The cells are attached to the bottom of the flasks, so they did not come out. Five days after the medium change, the cells were getting too crowded and were subcultured. First, the BME and a bottle of Trypsin were heated in a water bath to 37° C. Next, one flask was taken out of the incubator and its medium was poured into a disposable flask. 5 milliliters of trypsin was added to the monolayer of cells in the flask for 15-30 seconds and then poured into a disposable flask. The flask was sealed tightly and put in the incubator for 10-15 minutes. The flask was taken out of the incubator and the cells slowly slid down the side onto the bottom when held upright. 5 milliliters of BME was added to the flask and the cells in medium were manually pipetted into a single cell suspension. Samples of 0.2 milliliters of the suspended cells were put into two new culture flasks containing 30 milliliters of BME (at 37° C.). The two new flasks were placed back in the incubator. This process of changing the medium and then subculturing was continued 4 times. Using a hemacytometer, the cells were counted to find out how many were in suspension per millimeter of medium. 15 milliliters of cells in medium were needed with a concentration of 5×10$^5$ cells/mL. After the 15 milliliters of cells in suspension were made, they were ready to be seeded onto the materials.

Step 3: Seeding the Cells

The cells were seeded onto a piece of material that was approximately 2.5 centimeters×2.5 centimeters (1 inch by 1 inch). Before the cells were added, the pieces of material were placed in a 24 millimeter well of a Transwell plate containing 6 wells per plate. For Examples 1-3 the membrane in the well was removed with a sterile razor blade, for Comparative Example C1 the membrane was kept in and no fiber material was added. This membrane was made of polycarbonate with 0.4 micrometer pores. This is an ideal surface for the cells to grow on, and makes a good comparison. Two milliliters of BME was added to the bottom of the plate (below the material) and the piece of material was allowed to soak up the medium. Then, 1 milliliter of the cells in suspension was added to the top of the material. In order to keep the material from floating, the insert that came with the Transwell plates was placed on top of the well and material. The plates were covered and sealed with tape and placed in an incubator. 24 hours later, the plates were prepared to have SEM pictures taken.

Step 4: Analysis of Cell Growth Using SEM Micrographs

Each of the materials was studied by SEM Micrograph to determine if cell growth had occurred. The results are summarized in Table 1.

TABLE 1

| Example | Summary of SEM Micrograph |
|---|---|
| C1 | Cells attached normally. About half the cells were elongated, and they were spread out evenly on the membrane. The cells had clearly proliferated. |

TABLE 1-continued

| Example | Summary of SEM Micrograph |
|---|---|
| 1 | Cells were slightly less dense than C1. Attachment of the cells was present, but there are many more rounded cells than in C1 . . . |
| 2 | Cells were much less dense than in C1. Of the cells that were present, none of them were elongated to suggest good attachment to the material. |
| 3 | The cells were just as dense on this material as they were on C1. Some of the cells were attached, but more were rounded here than on C1. |

What is claimed is:

1. A method of culturing cells comprising:
providing a matrix of biaxially oriented, thermoplastic film substrate having a schistose surface, the matrix dispersed in a cell culture medium; and
inoculating the matrix with cells, allowing for cell growth and attachment within the thickness of the matrix.

2. The method of claim 1, wherein the schistose surface comprises microflakes having an average length of less than 20 micrometers, an average width of less than 200 micrometers, and an average thickness of 1 to 20 micrometers.

3. The method of claim 2, wherein the microflakes have an aspect ratio of the surface from 1:1 to 1:20.

4. The method of claim 2, wherein the microflakes have a surface area greater than 0.5 m$^2$/gram.

5. The method of claim 1, wherein the matrix comprises a melt-processible immiscible mixture of a semicrystalline polymer component and a void-initiating component.

6. The method of claim 1, wherein the matrix of biaxially oriented, thermoplastic film substrate comprises a polyolefin.

7. The method of claim 6, wherein the polyolefin is selected from polyethylene homopolymer, polypropylene homopolymer, copolymers of polyethylene, copolymers of polypropylene, blends comprising polypropylene, and blends comprising polyethylene.

8. The method of claim 1, wherein the matrix of biaxially oriented, thermoplastic film substrate comprises an aliphatic polyester.

9. The method of claim 8, wherein the aliphatic polyester is selected from poly(butylene succinate) homopolymer, poly(butylene adipate) homopolymer, poly(butylene adipate-succinate) copolymer, poly(ethylene succinate-adipate) copolymer, poly(ethylene adipate) homopolymer, polylactide, polydioxanone, polycaprolactone, poly(3-hydroxybutyrate), poly(3-hydroxyvalerate), polyglycolide, poly(oxyethylene glycolate), copolymers of polylactide, and copolymers of polyglycolide.

10. The method of claim 1, wherein the matrix of biaxially oriented, thermoplastic film substrate comprises a blend of two or more polymers.

11. The method of claim 1, wherein the cells are selected from mammalian cells, bacteria and fungi.

12. The method of claim 11, wherein the cells are fibroblasts.

13. The method of claim 1 wherein the schistose surface comprises an integral matrix of biaxially oriented, thermoplastic microflakes.

* * * * *